United States Patent
Dziuron et al.

Patent Number: 6,036,492
Date of Patent: Mar. 14, 2000

[54] COLLECTION OF ARTIFICIAL FRONT TEETH

[75] Inventors: Peter Dziuron, Lutjenburg; Markus Firla, Hasbergen-Gaste, both of Germany

[73] Assignee: Zahnfabrik Werchan Dental GmbH, Lutjenburg, Germany

[21] Appl. No.: 09/180,882

[22] PCT Filed: Mar. 31, 1998

[86] PCT No.: PCT/EP98/01859

§ 371 Date: Nov. 24, 1998

§ 102(e) Date: Nov. 24, 1998

[87] PCT Pub. No.: WO98/44866

PCT Pub. Date: Oct. 15, 1998

[30] Foreign Application Priority Data

Apr. 7, 1997 [DE] Germany .................. 197 14 282

[51] Int. Cl.[7] .................................................. A61C 13/08
[52] U.S. Cl. ........................................ 433/202.1; 433/197
[58] Field of Search ................ 433/26, 197, 202.1, 433/203.1, 167

[56] References Cited

U.S. PATENT DOCUMENTS 1,338,068  4/1920  Bush .
2,449,435  9/1948  Whittemore ............................... 32/71
4,909,738  3/1990  Ai et al. .................................... 433/202.1
5,639,235  6/1997  Lapointe et al. ......................... 433/26

OTHER PUBLICATIONS

Trubyte Bioblend Publication, 1961.

Trubyte Bioform Publication, 1958.

*Primary Examiner*—Nicholas D. Lucchesi
*Attorney, Agent, or Firm*—Alix, Yale & Ristas, LLP

[57] ABSTRACT

Collection of artificial front teeth which, in important sizes classes, comprises three groups of shapes which differ in terms of the relationships of the mesiodistal widths of their vestibular surfaces in the cervical, central and incisal thirds of their length, namely: a cervically accentuated group in which the said widths are approximately identical, a centrally accentuated group in which the width in the central third is greater than the width in the cervical third by at least the factor 1.15, and the width in the incisal third is not greater than the width in the central third, and an incisally accentuated group in which the width in the incisal third is greater than the width in the cervical third at least by the factor 1.18 and the width in the central third is smaller than the width in the incisal third.

6 Claims, 1 Drawing Sheet

COLLECTION OF ARTIFICIAL FRONT TEETH

CROSS REFERENCE TO RELATED APPLICATION

This is the U.S. national phase of International Application No. PCT/EP98/01859 filed Mar. 31, 1998.

BACKGROUND OF THE INVENTION

The efforts that have been made to simulate as closely as possible the wide variety of shapes of the natural teeth have led to a situation where the collections of artificial front teeth available on the market comprise a very large number of individual tooth shapes. This not only complicates matters in terms of manufacture and storage, but also makes selection difficult because of the profusion of different types. The categories chosen for these collections are also unsatisfactory. These are, on the one hand, categories based on the Kretschmer constitutional type classification which proposes correspondences between the tooth shape and the athletic, pyknic and leptosomic constitutional types, and, on the other hand, the association with geometric figures such as triangle, rectangle, shovel shape, square, oval, which are only to be found with difficulty in the multiplicity of shapes of natural teeth.

SUMMARY OF THE INVENTION

The invention creates a classification of a collection of artificial teeth, linked to certain tooth dimensions, which can be easily measured, but are also easy to evaluate by the trained eye.

The collection of artificial front teeth according to the invention comprises, in each important size class, three groups of shapes which differ in terms of the relationships of the mesiodistal widths of their vestibular surfaces in the cervical, central and incisal thirds of their length. In a cervically accentuated group, the mesiodistal widths are approximately identical in all the thirds. That is to say they differ from one another by not more than 10%, preferably 5%. In a centrally accentuated group, the width of the tooth in the central third is greater than in the two other thirds, and in particular it is greater than the width in the cervical third at least by the factor 1.15, preferably 1.2. In an incisally accentuated group, the width in the incisal third is greater than in the two other thirds, and in particular greater than the width in the cervical third by the factor 1.18, preferably 1.24.

The front teeth are the incisors and canines. With respect to the width measurement according to the invention, the vestibular surfaces are delimited by their margins. These can be visualized without difficulty. The border lines forming the basis of the width measurement are defined by the lines of greatest curvature (smallest radius of curvature in the horizontal sectional plane). The width is not to be measured linearly, but following the curved surface, and in particular along that line which connects by the shortest distance two points, each situated at the same height, of the two border lines.

The thirds are determined by dividing by three the length of the vestibular surfaces between the cutting edge and the cervical margin of the enamel measured along their midline. In each third, measurement is carried out at the area of greatest width. This may coincide with a border line of the third.

The invention relates exclusively to artificial teeth in the real sense, i.e. mechanically produced front teeth which imitate fully anatomically the shapes of the human front teeth and are used as replacements in edentulous areas of the jaw in the context of prosthetic replacement by total or partial prostheses and implant superstructures. It does not relate to crowns.

BRIEF DESCRIPTION OF A THE DRAWING

The invention is explained in greater detail below with reference to the drawing, in which:

FIG. 1 shows the vestibular surface of a tooth, showing the measurement points and the dividing lines, and FIGS. 2 to 4 show three different types of teeth.

DETAILED DESCRIPTION OF THE PREFERRED EMBODIMENT

Figure 1:
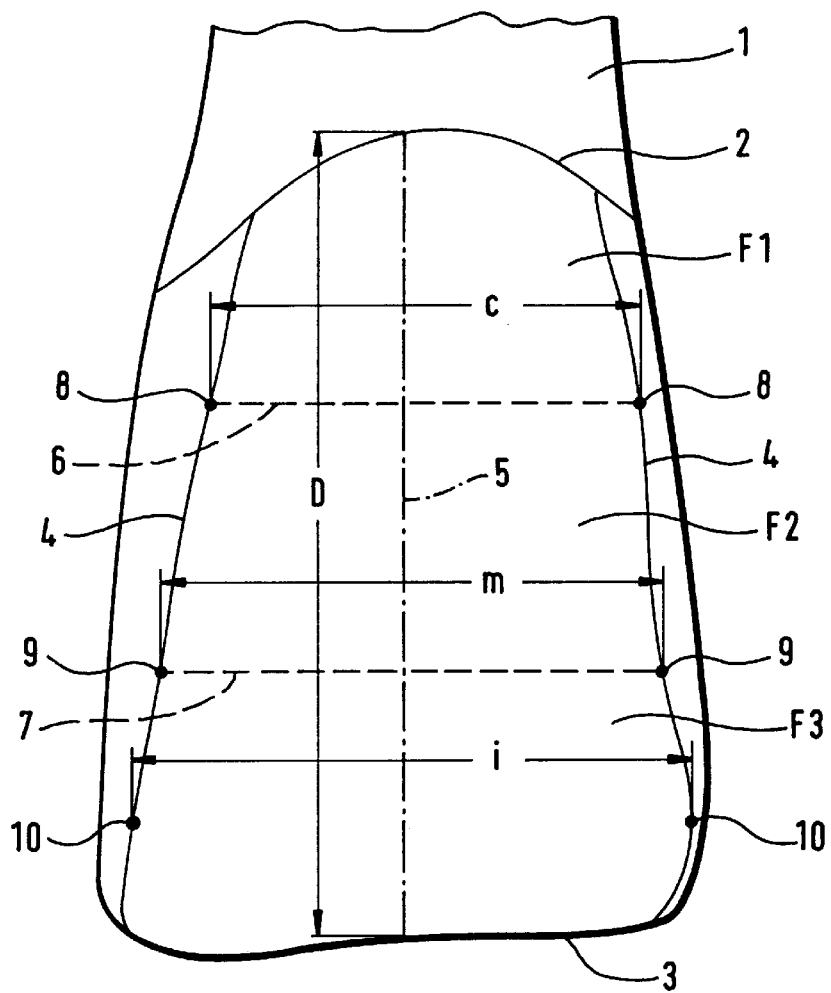

FIG. 1, representing an upper incisor, shows the tooth neck 1, the cemento-enamel limit 2 of the enamel, the cutting edge 3 and the vestibular margins 4 which are defined by the lines of in each case the smallest radius of curvature in planes running perpendicular to the tooth axis. The line 5 represents the mid-line of the vestibular surface thus delimited. Its length between the enamel margin 2 and the cutting edge 3 is divided into three equal sections, their limits 6, 7 being perpendicular to the tooth axis. They separate the cervical third F1 from the central third F2 and separate the latter from the incisal third F3.

The greatest mesiodistal width in each of these sections is determined. In the example shown (FIG. 1), this lies at the line 10 in the incisal third F3. The width is to be measured between its end points 10. The same applies to the central third, in which the greatest mesiodistal width is determined between the measurement points 9. In the cervical third F1, the measurement is carried out between the points 8. The greatest width measured in the cervical third is designated by the symbol "c", that measured in the central third is designated by the symbol "m" and that measured in the incisal third is designated by the symbol "i".

On measuring a large number of natural teeth, it was found that the criterion of width comparison in the three thirds afforded a particularly simple and clear standardization and a collection of artificial teeth which covers the necessary range of types with a comparatively small number of different tooth shapes, provided that the tooth groups representing these types are characterized and distinguished from each other as has been set out above and in the claims.

Figure 2:
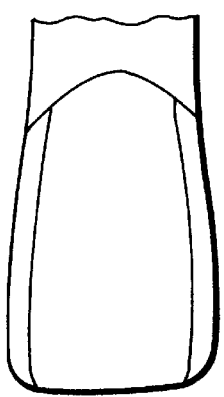

The group of cervically accentuated teeth is characterized by the fact that c, m and i are approximately identical or differ from one another by not more than 10%, preferably 5%. FIG. 2 shows an example.

Figure 3:
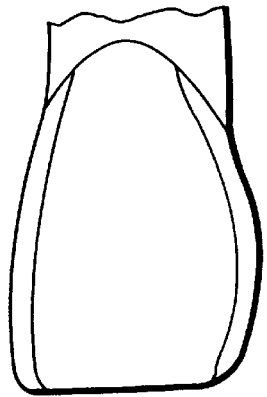

The centrally accentuated group, which is represented by way of example in FIG. 3, is characterized by the fact that a sturdy body shape determines the appearance. It is therefore also referred to as body-accentuated. Its greatest mesiodistal width lies in the central third. This is greater than in the incisal third and considerably greater (namely at least by the factor 1.15, preferably 1.2) than the greatest width of the cervical third.

Figure 4:
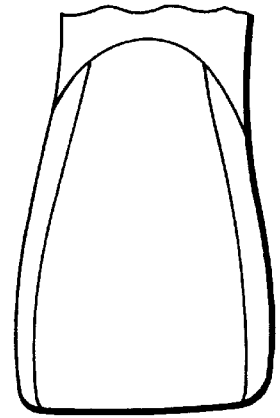

The incisally accentuated group, which is represented by FIG. 4, shows its greatest width in the incisal third. It is greater there than in the central third and considerably greater (namely at least by the factor 1.18, preferably 1.24) than in the cervical third.

This grouping in threes is found in the collection according to the invention for each critical size class, of which at least three are expediently provided, designated by I, M and S. Preferably, it is also provided in additional size classes; this is not absolutely necessary, however.

The following table shows, for the size class "L" (large), the corresponding widths in the different thirds. The letters "C", "B" and "I" stand for the cervically accentuated, body-accentuated and incisally accentuated groups. In addition to the maximum mesiodistal spacings on the vestibular surface, the respective heights "D" of the vestibular surfaces are also indicated.

| | | Maximum mesiodistal spacing on the vestibular surface in mm | | | |
|---|---|---|---|---|---|
| | | F1 | F2 | F3 | D |
| | | Upper jaw | | | |
| Tooth 11 | CL | 9.0 | 9.0 | 9.1 | 11.1 |
| Tooth 21 | CL | 8.3 | 8.3 | 8.3 | 11.0 |
| Tooth 11 | BL | 7.8 | 9.4 | 9.2 | 11.6 |
| Tooth 21 | BL | 7.2 | 9.2 | 8.2 | 11.7 |
| Tooth 11 | IL | 7.6 | 8.3 | 8.7 | 11.7 |
| Tooth 21 | IL | 7.0 | 8.0 | 9.0 | 11.6 |
| Tooth 12 | CL | 7.9 | 7.8 | 7.8 | 10.1 |
| Tooth 22 | CL | 7.7 | 7.8 | 7.8 | 10.0 |
| Tooth 12 | BL | 5.8 | 7.8 | 6.8 | 10.4 |
| Tooth 22 | BL | 5.6 | 7.2 | 7.0 | 10.3 |
| Tooth 12 | IL | 5.9 | 7.1 | 7.2 | 10.3 |
| Tooth 22 | JL | 5.8 | 7.2 | 7.5 | 10.4 |
| Tooth 13 | CL | 9.1 | 9.1 | 9.1 | 12.5 |
| Tooth 23 | CL | 9.8 | 9.7 | 9.6 | 12.3 |
| Tooth 13 | BL | 8.0 | 8.8 | 8.8 | 12.8 |
| Tooth 23 | BL | 7.8 | 9.4 | 9.2 | 12.0 |
| Tooth 13 | IL | 7.2 | 9.3 | 9.5 | 12.3 |
| Tooth 23 | IL | 7.5 | 9.4 | 9.5 | 12.0 |
| | | Lower jaw | | | |
| Tooth 31 | CL | 7.3 | 7.1 | 6.9 | 9.0 |
| Tooth 41 | CL | 6.9 | 6.9 | 6.8 | 8.8 |
| Tooth 31 | BL | 6.2 | 7.2 | 7.0 | 8.7 |
| Tooth 41 | BL | 5.6 | 7.0 | 6.2 | 8.8 |
| Tooth 31 | IL | 5.0 | 5.6 | 6.2 | 8.7 |
| Tooth 41 | IL | 5.1 | 5.9 | 6.4 | 8.9 |
| Tooth 32 | CL | 6.0 | 6.0 | 6.0 | 9.3 |
| Tooth 42 | CL | 6.8 | 6.8 | 6.8 | 9.0 |
| Tooth 42 | BL | 6.1 | 7.7 | 7.4 | 10.0 |
| Tooth 32 | BL | 5.9 | 7.5 | 7.3 | 9.7 |
| Tooth 32 | IL | 5.2 | 6.1 | 6.5 | 9.8 |
| Tooth 42 | IL | 5.1 | 6.3 | 6.5 | 9.9 |
| Tooth 33 | CL | 7.5 | 7.4 | 7.4 | 11.0 |
| Tooth 43 | CL | 8.0 | 7.7 | 7.5 | 10.7 |
| Tooth 33 | BL | 7.0 | 8.8 | 7.8 | 10.7 |
| Tooth 43 | BL | 7.0 | 8.6 | 8.0 | 10.4 |
| Tooth 33 | IL | 7.5 | 8.2 | 9.5 | 12.2 |
| Tooth 43 | IL | 7.5 | 9.0 | 9.3 | 12.5 |

The following table gives a numerical example for an upper cervically accentuated incisor in three size classes:

| | | Maximum mesiodistal spacing on the vestibular surface in mm | | | |
|---|---|---|---|---|---|
| | | F1 | F2 | F3 | D |
| Tooth 21 | CL | 8.3 | 8.3 | 8.3 | 11.1 |
| Tooth 21 | CM | 8.0 | 7.9 | 7.9 | 10.6 |
| Tooth 21 | CS | 7.5 | 7.5 | 7.4 | 10.0 |

We claim:

1. Collection of artificial front teeth comprising three groups of shapes with the teeth in each group having a vestibular surface with a longitudinal mid-line extending between a cervical margin and a cutting edge and cervical, central and incisal portions of substantially equal length along the mid-line, each of said portions having a separate mesiodistal width, said groups comprising:

a cervically accentuated group in which the cervical mesiodistal width and the incisal mesiodistal width differ from the central mesiodistal width by not more than 10%, a centrally accentuated group in which the central mesiodistal width is greater than the cervical mesiodistal width at least by 15%, and the incisal mesiodistal width is not greater than the central mesiodistal width, and an incisally accentuated group in which the incisal mesiodistal width is greater than the cervical mesiodistal width at least by 18%, and the central mesiodistal width is smaller than the incisal mesiodistal width.

2. Collection of artificial front teeth according to claim 1, characterized in that the mesiodistal width in each portion is the largest width in that portion.

3. Collection of artificial front teeth according to claim 1, characterized in that the mesiodistal width in each portion is the average width of that portion.

4. Collection of artificial front teeth according to claim 1 characterized in that, in the cervically accentuated group, the cervical and incisal mesiodistal widths differ from the central mesiodistal width by not more than 5%.

5. Collection of artificial front teeth according to claim 1, characterized in that in the centrally accentuated group the central mesiodistal width is greater than the cervical mesiodistal width at least by 20%.

6. Collection of artificial front teeth according to claim 1, characterized in that in the incisally accentuated group the incisal mesiodistal width is greater than the cervical mesiodistal width by at least 24%.

* * * * *